United States Patent [19]

Musicant et al.

[11] Patent Number: 5,063,907
[45] Date of Patent: Nov. 12, 1991

[54] DISPOSABLE AND/OR STERILIZABLE CUSHIONING DEVICE FOR A LARYNGOSCOPE

[76] Inventors: Belmont S. Musicant, 3260 Club Dr., Los Angeles, Calif. 90064; William W. Musicant, 17650 Tarzana St., Encino, Calif. 91316

[21] Appl. No.: 366,140

[22] Filed: Jun. 14, 1989

[51] Int. Cl.$^5$ .............................................. A61B 1/26
[52] U.S. Cl. ....................................... 128/10; 128/11
[58] Field of Search ................ 30/151, 285, 286, 284, 30/77, 78, 51–53; 128/10, 11, 200.26; 224/232, 233; 56/298

[56] References Cited

U.S. PATENT DOCUMENTS

| 3,329,188 | 7/1967 | McCord | 30/286 |
| 3,381,807 | 5/1968 | Vaughn | 224/232 |
| 3,388,467 | 6/1968 | Martin | 30/53 |
| 4,579,108 | 4/1986 | Bauman | 128/10 |
| 4,834,077 | 5/1989 | Sun | 128/11 |

FOREIGN PATENT DOCUMENTS 1082530 12/1954 France .................... 30/285

*Primary Examiner*—Edward M. Coven
*Assistant Examiner*—Martin S. Graham
*Attorney, Agent, or Firm*—W. Edward Johansen

[57] ABSTRACT

A disposable and/or sterilizable cushioning device is used with a plurality of different types of laryngoscopes. Each laryngoscope includes a blade having a lateral shelf which has a top surface land-area which may come into contact with a patient's teeth, gums and lips, causing dental damage or possibly the bruising of his gums and/or his lips. The disposable and/or sterilizable cushioning device includes an elongated clip which is formed from a soft and resilient material and which wraps snugly around the top surface land-area of the blade, where the elongated clip comes in contact with a patient's teeth or his gums thereby protecting his teeth and gums the elongated clip having a first side surface, a second side surface, a bottom surface and a top surface and which has a longitudinal slit on the bottom surface adjacent to the first side surface. The elongated clip is slidably and/or removaly installed to the top surface land-area of the blade so that the bottom surface is adjacent to the top surface land-area. The disposable and/or sterilizable cushioning device protects the upper teeth, lips and gums of the patient by cushioning any pressure or contact with upper teeth, lips and gums during endotracheal intubation.

1 Claim, 2 Drawing Sheets

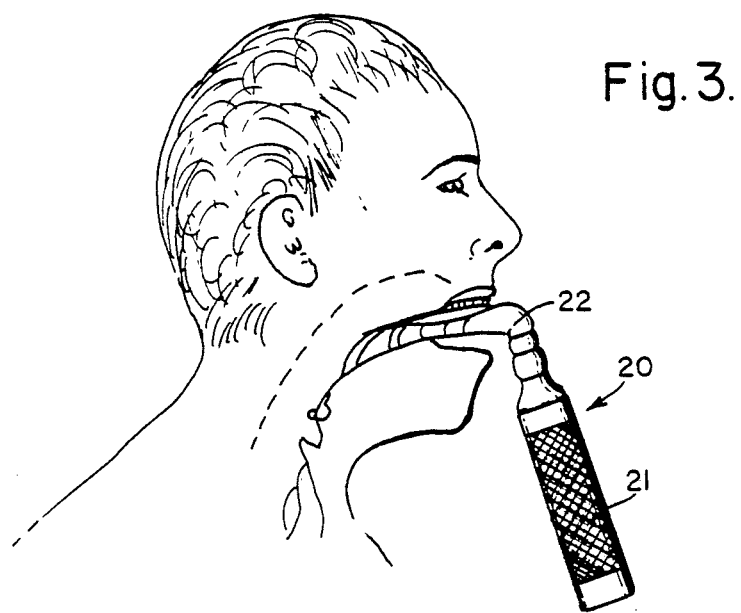
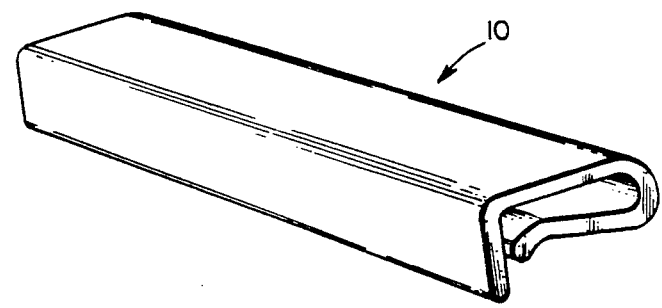
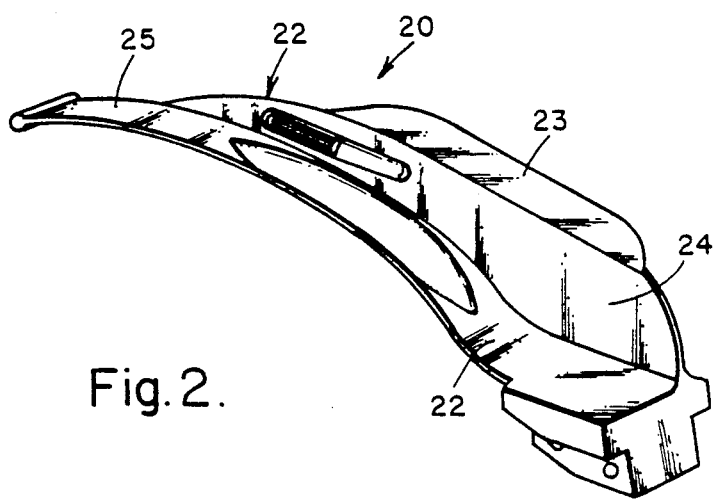
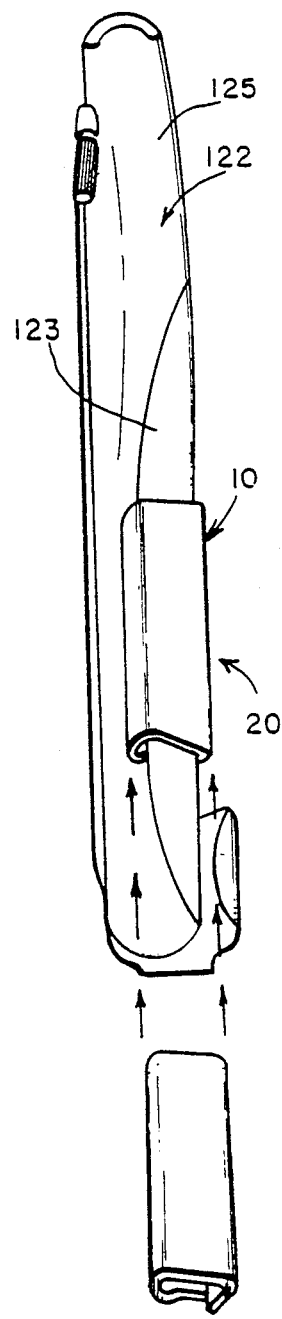

Fig. 5.
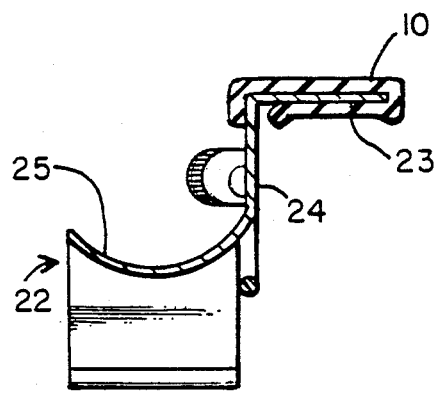
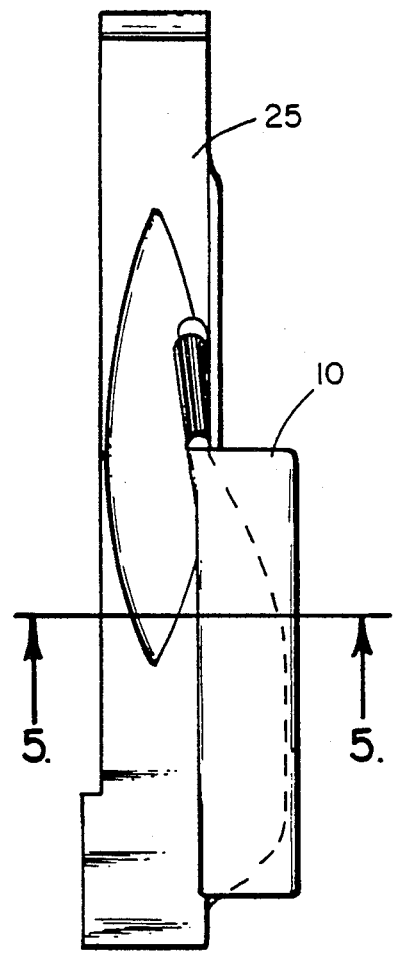
Fig. 4.

DISPOSABLE AND/OR STERILIZABLE CUSHIONING DEVICE FOR A LARYNGOSCOPE

BACKGROUND OF THE INVENTION

1. Field of the Inventions

The present invention relates to a disposable and/or sterilizable cushioning device for a laryngoscope for use in protecting the upper teeth, gums and lips of a patient who is undergoing an endotracheal intubation and more particularly to a cushioning device which is of one piece construction thereby requiring no assembly and is color coded by size for the anesthesiologist's ease and speed of choice in fitting all sizes of laryngoscope.

2. Description of the Prior Art

Although there is a risk of possible damage to the upper teeth of patients, laryngoscopes are routinely used to facilitate endotracheal intubation such as during surgery to permit the patients to breathe and/or to administer anesthesia. In addition, laryngoscopes are utilized to displace the tongue and epiglottis thereby permitting direct visualization of the glottis through the mouth opening. The standard method for performing intubation involves placing a patient in a supine position, tilting his head backward as far as possible and distending his lower jaw to open his mouth widely. A rigid blade, which can be straight or slightly curved, then is inserted through his mouth into his throat passageway to displace the tongue and epiglottis thereby exposing the glottis. Thereafter, the desired visual observation can be achieved, then the endotracheal tube may be placed through the glottis and the anesthetic can be applied and/or the mechanical ventilation may be effected. There is always a risk of damage to the upper teeth, gums & lips, of patients, laryngoscopes are commonly used to facilitate endotracheal intubation while in surgery to permit the patients to breathe and/or to administer anesthesia. Laryngoscopes are designed to move the tongue and epiglottis so the anesthesiologist can have direct visualization of the glottis through the mouth opening. The standard method for performing intubation involves placing a patient in a supine position, tilting his head backward as far as possible and distending the lower jaw to open the mouth widely. A rigid blade, which can be straight or slightly curved, then is inserted through the mouth into the throat passageway to displace the tongue and epiglottis thereby exposing the glottis. Thereafter, the desired visual observation can be achieved, the anesthetic can be applied and/or the mechanical ventilation may be effected.

U.S. Pat. No. 4,583,527, entitled Disposable Cushioning Device for a Laryngoscope, issued to Belmont S. Musicant and William W. Musicant on Apr. 22, 1986, teaches a disposable cushioning device for use with a laryngoscope which includes a handle and a blade. The handle contains a battery which is connected to a first electrical contact pad on the upper surface of the handle. The blade has a lateral shelf which has a top surface, an upright wall and a blade portion extending in a direction opposite to the shelf. The blade portion is curved from its base to its tip which is in the form of a rounded transverse bar of the same width as the blade portion. The base of the blade portion is hinged to the top of the handle. The blade carries an electric lamp which is connected to a second electrical contact pad in the base of the blade portion. The disposable cushioning device is sterilizable and includes an elongated sheath which has a bottom surface and a top surface. The elongated sheath is slidably and removably coupled to the shelf of the blade so that the bottom surface is adjacent to the shelf. The disposable cushioning device also includes an elongated layer of soft pliable plastic material. An adhesive material adheres the elongated layer of soft pliable plastic material to the top surface of the elongated sheath. The disposable cushioning device protects the upper teeth of a patient undergoing an endotracheal intubation. 14 The disposable cushioning device of U.S. Pat. No. 4,583,527 is formed from two pieces and protects the teeth only. The disposable cushioning device incorporates the use of adhesives to bond piece the elongated sheath to the elongated layer of soft pliable plastic material to the top surface of the elongated sheath. Assembling the disposable cushioning device while prepping for an endotracheal intubation is not only unfeasible, but also time consuming and difficult to understand. The use of a strong glue, solvent, or adhesive will cause fumes which are possibly dangerous. These fumes would continue until the glue, solvent, or adhesive is dried or cured. The tedious and bothersome assembling of the disposable cushioning device would not be well received in the operating room due to the amount of time involved. The fumes which may be caused by either the glue or adhesive material are also undesirable. The disposable cushioning device may come apart during intubation and possibly block the patient's airway, if it has not been assembled properly. All medical professionals, especially ones who earn their living either in operating rooms or by handling emergencies will not have the time to assemble the disposable cushioning device and should not be required to do so. Most anesthesiologists have heavy workloads and must be alert at all times when a patient is under endotracheal intubation. The disposable cushioning device could possibly be a hazard and as such most medical professionals would choose not to use the disposable cushioning device. Time is unknown when it deals with either emergencies or other medical reasons for immediate surgery, which call for a patient to be intubated right away, not allowing for possible hazardous fumes which could possibly have a very negative effect on a patient whom is already in a weakened state. When the disposable cushioning device is attached to a straight blade it has only one of two contact points which come into contact with the teeth. This could be a dangerous situation because of a teeth-to-metal contact on one side of blade may cause uneven pressure on the teeth which might possibly chip a tooth.

U.S. Pat. No. 4,295,465, entitled Laryngoscope Blade, issued to Gabor Racz and Forrest Allen on Oct. 20, 1981, teaches a blade for a laryngoscope which includes a base portion and projecting flange portion. The flange portion extends along part of the base portion and is pivotally mounted with respect thereto. A biasing mechanism provides a preselected bias force on the flange portion to hold the flange portion in projecting position. If in using the laryngoscope blade the flange portion contacts the patient's upper teeth, the flange portion pivots when the force applied exceeds the predetermined bias force.

U.S. Pat. No. 4,384,570, entitled Laryngoscope, issued to John T. Roberts on May 24, 1983, teaches a laryngoscope which includes a blade and a handle having a rigid handle section and a movable handle section. The movable handle section is adapted to be pivoted and locked at a desired position relative to the rigid handle section prior to use with a patient.

U.S. Pat. No. 4,350,154, entitled Teeth Protecting Device, issued to Elliot V. Feldbau on Sept. 21, 1982, teaches a teeth protecting device which is structured to cling to the teeth with sufficient tenacity so that the teeth protecting device is remains secure throughout oral exploration and/or corrective measures and yet so that the teeth protecting device is removable without dislodging pre-existing dental repair work and/or weakly anchored teeth. The provision of mouth-protecting and/or teeth protecting devices for dental, medical and athletic purposes are described in the following patents: U.S. Pat. Nos. 2,705,492, 3,016,052, 3,124,129, 3,236,235, 3,513,838, 3,864,832.

U.S. Pat. No. 3,766,909, entitled Laryngoscope with Disposable Blade and Light Guide, issued to Ahmet M. Ozbey on Oct. 23, 1973, teaches a laryngoscope which includes a wireless, disposable blade containing a relatively stiff light guide for transmitting light from a light source which is associated with the handle to a point substantially midway between the ends of an upper curved section of the disposable blade. The disposable blade is formed of a relatively soft plastic material and has a straight light guide. An adaptor connects the disposable blade to the handle and which mounts the light source in a position adjacent one end of the light guide.

U.S. Pat. No. 3,426,749, entitled Disposable Cover for Laryngoscope Blade, issued to John Anthony Jephcott on Feb. 11, 1969, teaches a disposable cover for a laryngoscope blade. The disposable cover is formed of pre-sterilized, translucent material and is adapted to be pulled over the laryngoscope blade.

U.S. Pat. No. 3,507,272, entitled Laryngoscope, issued to Asmund S. Laerdal on Apr. 21, 1970, teaches a laryngoscope blade which is formed of soft plastic material and upon which a light source is mounted near the distal end of the laryngoscope blade.

U.S. Pat. No. 4,432,350, entitled Means for Applying Topical Anesthesia for Use with a Laryngoscope, issued to Alan J. Breslau and Bernard Broad on Feb. 21, 1984, teaches a laryngoscope which includes a device for applying topical anesthesia.

U.S. Pat. No. 4,437,458, entitled Laryngoscope, issued to Michael S. Upster on Mar. 20, 1984, teaches a laryngoscope which includes a blade which is curved and tubular and which has an improved lighting mechanism for illuminating the forward end of the blade.

U.S. Pat. No. 2,354,471, entitled Laryngoscope, issued to Robert R. MacIntosh on Aug. 18, 1943, teaches a laryngoscope which includes a blade which is curved.

U.S. Pat. No. 2,289,226, entitled Laryngeal Speculum, issued to Richard von Fogregger on July 7, 1942, teaches a laryngoscope which includes a blade which is straight.

U.S. Pat. No. 2,646,036, entitled Foldable and Separable Laryngoscope, issued to William G. Allyn and Charles Sewell Cook on July 21, 1953, teaches a foldable and separable laryngoscope which includes a blade which is straight.

U.S. Pat. No. 4,425,909, entitled Laryngoscope, issued to Michael J. Rieser on Jan. 17, 1984, teaches an improved laryngeal speculum for examining the throat and larynx of a patient. The laryngeal speculum includes an elongated blade, an elongated handle and neck which interconnects the elongated blade and the elongated handle. The neck is shaped, contoured and dimensioned such that when the elongated blade is positioned within the mouth and throat of a patient and lifting force exerted on the handle there will be no force applied to the upper teeth which have often been used as a fulcrum about which to rotate the handle thereby resulting in numerous broken teeth.

U.S. Pat. No. 4,406,280, entitled Laryngoscope including a Disposable Blade and its Method Use, issued to Michael S. Upster on Sept. 27, 1983, teaches a laryngoscope which includes a separate disposable blade.

U.S. Pat. No. 3,598,113, entitled Disposable Laryngoscope Construction, issued to William C. Moore on Aug. 10, 1971, teaches a disposable laryngoscope which includes a unitary plastic blade and handle assembly which includes a blade portion and a handle portion and which forms a disposable part. The handle portion of the unitary plastic blade and handle assembly is hollow and, when it is in use, contains a light unit which includes batteries, a lamp and an operating switch. The unitary plastic blade and hand assembly includes an optical fiber bundle for carrying light from the lamp within the handle portion to a point near the distal end of the blade portion. The light unit is not disposable and is removed for reuse before the unitary plastic blade and hand assembly is thrown away.

U.S. Pat. No. 4,550,717, entitled Throat Examination Device, issued to Karl Berger on Nov. 5, 1985, teaches a device which a physician uses in examining the throat of a patient.

U.S. Pat. No. 4,041,936, entitled Medical Implement, issued to Marcellina Diaz on Aug. 16, 1977, teaches a medical implement in the form of a tongue blade suitable for rendering first aid assistance to a seizure patient.

U.S. Pat. No. 3,771,514, entitled Laryngoscope, issued to John P. Huffman and Carl L. Foltz on Nov. 13, 1973, teaches a laryngoscope which allows concurrent direct and indirect viewing of the larynx, especially when direct viewing is difficult. Such indirect viewing is permitted by the use of a prism which is formed out of a plastic material and which also functions as a "bite block".

SUMMARY OF THE INVENTION

In view of the foregoing factors and conditions which are characteristic of the prior art it is the primary object of the present invention to provide a disposable and/or sterilizable cushioning device for use with a laryngoscope which protects the upper teeth, gums and lips of a patient who is undergoing an endotracheal intubation.

It is another object of the present invention to provide a disposable and/or sterilizable cushioning device for use with a laryngoscope which is of one piece construction thereby requiring neither assembly nor potentially dangerous solvents or adhesives and is color coded by size for the anesthesiologist's ease and speed of choice in fitting all sizes of laryngoscope so that the disposable and/or sterilizable cushioning device does not need to be assembled, and it requires no adhesives or solvents the fumes of which might be hazardous to a patient.

It is still another object of the present invention to provide a disposable and/or cushioning device for use with a laryngoscope which is of one piece construction so that it will not fall apart while in use thereby possibly blocking the airway of a patient.

It is yet another object of the present invention to provide a disposable and/or sterilizable cushioning device for use with a laryngoscope which snugly wraps around the contact area of laryngoscope in order to protect the patient's teeth, gums and lips from contact with the blade of the laryngoscope.

In accordance with an embodiment of a disposable and/or sterilizable cushioning device for use with a plurality of different types of laryngoscopes is described. Each laryngoscope includes a blade having a lateral shelf which has top surface land-area which may come into contact with a patient's teeth, gums and lips, causing dental damage or possibly the bruising of his gums and/or his lips. The disposable and/or sterilizable cushioning device includes an elongated clip which is formed from a soft and resilient material and which wraps snugly around the top surface land-area of the blade, where the elongated clip comes in contact with a patient's teeth or his gums thereby protecting his teeth and gums the elongated clip having a first side surface, a second side surface, a bottom surface and a top surface and which has a longitudinal slit on the bottom surface adjacent to the first side surface. The elongated clip is slidably and/or removably installed to the top surface land-area of the blade so that the bottom surface is adjacent to the top surface land-area. The disposable and/or sterilizable cushioning device protects the upper teeth, lips and gums of the patient by cushioning any pressure or contact with upper teeth, lips and gums during endotracheal intubation.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE DRAWING

FIG. 1 is a perspective view of a disposable and/or sterilizable cushioning device which has been made in accordance with the principles of the present invention.

FIG. 2 is a perspective view of a curved blade of a first laryngoscope having a lateral shelf having a top surface land area, an upright wall and a blade portion extending in a direction opposite to the shelf wherein the blade portion is curved from its base to its tip.

FIG. 3 is a schematic drawing of the disposable and/or sterilizable cushioning device which is used with the first laryngoscope to protect the upper teeth, lips and gums of a patient undergoing an endotracheal intubation of FIG. 2.

FIG. 4 is a top plan of the curved blade of FIG. 2 which demonstrates the disposable and/or sterilizable cushioning device in place on the top surface land area of the curved blade of the first laryngoscope.

FIG. 5 is a transverse side view in cross-section of the disposable and/or sterilizable cushioning device which illustrates how the disposable and/or sterilizable cushioning device fits only the area of the blade which would come into contact with the patient's teeth and which also shows the top surface land area of the curved blade of the first laryngoscope of FIG. 2 taken along line 5—5 of FIG. 4.

FIG. 6 is a top plan view of the disposable and/or sterilizable cushioning device of FIG. 1 slidably coupled to the top surface land area of a straight blade of a second laryngoscope.

DESCRIPTION OF THE PREFERRED EMBODIMENT

In order to best understand the present invention it is necessary to refer to the following description of its preferred embodiment and a laryngoscope in conjunction with the accompanying drawing. Referring to FIG. 1 a disposable and/or sterilizable cushioning device 10 is used with a laryngoscope to protect the upper teeth, lips and gums of a patient undergoing an endotracheal intubation.

Referring to FIG. 2 a physician uses a first laryngoscope 20 which includes a handle 21 and a blade 22 to perform endotracheal intubation and which is described in U.S. Pat. No. 2,354,471. The handle 21 contains a battery which is connected to a first electrical contact pad on the upper surface of the handle 21. The blade 22 includes a lateral shelf 23, an upright wall 24 and a blade portion 25 which extends in a direction opposite to the lateral shelf 23. The blade portion 25 is curved from its base 26 to its tip 27, the latter being in the form of a rounded transverse bar of the same width as the blade portion 25. The lateral shelf 23 of the curved blade 22 of the first laryngoscope 20 has a top surface land-area which may come into contact with a patient's teeth, gums and lips, causing dental damage or possibly the bruising of his gums and/or his lips. The curvature of the blade portion 25 facilitates easy passage over the tongue and is advantageous in that it avoids depression of the tongue which otherwise might result in an appreciable restriction of the visible aperture of the larynx. The tongue is pushed to one side of the wall 24 and restrained in its movement by the lateral shelf 23. The base 26 of the blade portion 25 is hinged to the top of the handle 21. The blade 22 carries an electric lamp 28 which is connected to a second electrical contact pad in the base 26 of the blade portion 25. When the blade 22 is swung upwards in its operating position the first and second electric contact pads engage to close the circuit through which the electric lamp 28 is lighted in order to illuminate the interior of the mouth.

Referring to FIG. 3 in conjunction with FIG. 1, FIG. 2, FIG. 4 and FIG. 5 the disposable and/or sterilizable cushioning device 10 may be used with a plurality of different types of laryngoscopes, including the first laryngoscope 20. The disposable and/or sterilizable cushioning device 10 includes an elongated clip 29 which is formed from a soft and resilient material and which wraps snugly around the top surface land-area of the blade, where the elongated clip comes in contact with a patient's teeth or his gums thereby protecting his teeth and gums. The elongated clip 29 has a first side surface 31, a second side surface 32, a bottom surface 33 and a top surface 34 and which has a longitudinal slit 35 on the bottom surface 33 adjacent to the first side surface 31. The elongated clip is slidably and/or removably installed to the top surface land-area of the curved blade 22 so that the bottom surface 32 is adjacent to the top surface land-area. The disposable and/or sterilizable cushioning device 10 protects the upper teeth, lips and gums of the patient by cushioning any pressure or contact with upper teeth, lips and gums.

Referring to FIG. 6 the disposable and/or sterilizable cushioning device 10 is used with a second laryngoscope 120 to protect the upper teeth, lips and gums of a patient undergoing an endotracheal intubation. The second laryngoscope 120 which includes a handle 121 and a blade 122 to perform endotracheal intubation.

The handle 121 contains a battery which is connected to a first electrical contact pad on the upper surface of the handle 121. The blade 122 includes a lateral shelf 123, an upright wall 124 and a blade portion 125 which extends in a direction opposite to the lateral shelf 123. The blade portion 125 is straight from its base 126 to of its tip 127, the latter being in the form of a transverse bar of the same width as the blade portion 125. The blade portion 125 facilitates easy passage over the tongue and is advantageous in that it avoids depression of the tongue which otherwise might result in an appreciable restriction of the visible aperture of the larynx. The base 126 of the blade portion 125 is hinged to the top of the handle 121. The blade 122 carries an electric lamp 128 which is connected to a second electrical contact pad in the base 126 of the blade portion 125. When the blade 122 is swung upwards in its operating position the first and second electric contact pads engage to close the circuit through which the electric lamp 128 is lighted in order to illuminate the interior of the mouth.

From the foregoing it can be seen that a disposable and/or sterilizable cushioning device for use in combination with a laryngoscope for protecting a patient's upper teeth, gums and lips from damage caused by the blade of the laryngoscope during an endotracheal intubation has been described.

It should be noted that the sketches are not drawn to scale and that distance of and between the figures are not to be considered significant.

What is claimed is:

1. A disposable and/or sterilizable cushioning device for use with a plurality of different types of laryngoscopes each of which includes a blade having a lateral shelf which has a top surface land-area which may come into contact with a patient's teeth, gums and lips, causing dental damage or possibly the bruising of his gums and/or his lips, said disposable and/or sterilizable cushioning device comprising:

a. an elongated clip which is formed from a soft and resilient material and which is adapted to wrap snugly around the top surface land area of the blade whereby said elongated clip comes in contact with a patient's teeth or his gums thereby protecting his teeth and gums, said elongated clip having a first side surface, a second side surface, a bottom surface and a top surface and also having a longitudinal slit on said bottom surface adjacent to said first side surface, said elongated clip adapted to be slidably and/or removably installed to the top surface land-area of the blade so that said bottom surface is adjacent to the top surface land area whereby said disposable and/or sterilizable cushioning device protects the upper teeth, lips and gums of the patient by cushioning any pressure or contact with upper teeth, lips and gums during endotracheal intubation.

* * * * *